United States Patent
Lev-Tov et al.

(10) Patent No.: US 12,373,965 B2
(45) Date of Patent: Jul. 29, 2025

(54) REGISTRATION OF TIME-SEPARATED X-RAY IMAGES

(71) Applicant: Mazor Robotics Ltd., Caesarea (IL)

(72) Inventors: Amir Lev-Tov, Tel Aviv (IL); Shay Shimon Peretz, Tel Aviv (IL); Yaniv Ben Zriham, Binyamina (IL); Moshe Shoham, Hoshaya (IL)

(73) Assignee: Mazor Robotics Ltd., Caesarea (IL)

( * ) Notice: Subject to any disclaimer, the term of this patent is extended or adjusted under 35 U.S.C. 154(b) by 500 days.

(21) Appl. No.: 17/526,935

(22) Filed: Nov. 15, 2021

(65) Prior Publication Data

US 2022/0189047 A1 Jun. 16, 2022

Related U.S. Application Data

(60) Provisional application No. 63/125,822, filed on Dec. 15, 2020.

(51) Int. Cl.
*G06T 7/38* (2017.01)
*G06T 7/215* (2017.01)
(Continued)

(52) U.S. Cl.
CPC ............ *G06T 7/38* (2017.01); *G06T 7/215* (2017.01); *G06T 7/337* (2017.01); *G06V 10/25* (2022.01);
(Continued)

(58) Field of Classification Search
None
See application file for complete search history.

(56) References Cited

U.S. PATENT DOCUMENTS

| 7,855,723 | B2 | 12/2010 | Preiss et al. |
| 8,218,905 | B2 | 7/2012 | Dekel et al. |

(Continued)

FOREIGN PATENT DOCUMENTS

| EP | 1968015 | 9/2008 | |
| EP | 1968015 A1 * | 9/2008 | ........... G06T 3/0068 |

(Continued)

OTHER PUBLICATIONS

El-Zahraa et al. "Current trends in medical image registration and fusion," Egyptian Informatics Journal, 2016, vol. 17, pp. 99-124.
(Continued)

*Primary Examiner* — Vincent Rudolph
*Assistant Examiner* — Meredith Taylor
(74) *Attorney, Agent, or Firm* — Sheridan Ross P.C.

(57) ABSTRACT

A method according to one embodiment of the present disclosure comprises receiving a first image of a patient's anatomy, the first image generated at a first time and depicting a plurality of rigid elements; receiving a second image of the patient's anatomy, the second image generated at a second time after the first time and depicting the plurality of rigid elements; determining a transformation from the first image to the second image for each one of the plurality of rigid elements to yield a set of transformations; calculating a homography for each transformation in the set of transformations to yield a set of homographies; and identifying, using the set of homographies, a common
(Continued)

portion of each transformation attributable to a change in camera pose, and an individual portion of each transformation attributable to a change in rigid element pose.

20 Claims, 5 Drawing Sheets

(51) Int. Cl.
   *G06T 7/33* (2017.01)
   *G06V 10/25* (2022.01)
   *G16H 30/20* (2018.01)
   *G16H 30/40* (2018.01)

(52) U.S. Cl.
   CPC ............. *G16H 30/20* (2018.01); *G16H 30/40* (2018.01); *G06T 2207/10116* (2013.01); *G06T 2207/30244* (2013.01); *G06V 2201/033* (2022.01)

(56) References Cited

U.S. PATENT DOCUMENTS

| | | | |
|---|---|---|---|
| 8,676,298 | B2 | 3/2014 | Wang et al. |
| 8,724,865 | B2 | 5/2014 | Hipp et al. |
| 9,265,463 | B1 | 2/2016 | Hipp et al. |
| 9,561,004 | B2 | 2/2017 | Forsberg |
| 9,901,407 | B2 | 2/2018 | Breisacher et al. |
| 2008/0262345 | A1 | 10/2008 | Fichtinger et al. |
| 2017/0091919 | A1* | 3/2017 | Karino ................. G06V 20/653 |
| 2017/0119316 | A1 | 5/2017 | Herrmann et al. |
| 2017/0273614 | A1 | 9/2017 | Giphart et al. |
| 2020/0058098 | A1 | 2/2020 | Hirakawa |

FOREIGN PATENT DOCUMENTS

| | | | |
|---|---|---|---|
| EP | 3714792 | 9/2020 | |
| EP | 3714792 A1 * | 9/2020 | ........... A61B 6/4441 |
| WO | WO 2019/102473 | 5/2019 | |

OTHER PUBLICATIONS

Forsberg et al. "Model-based registration for assessment of spinal deformities in idiopathic scoliosis," Physics in Medicine and Biology, vol. 59, No. 2, pp. 311-326.

Hill et al. "Medical image registration," Physics in Medicine and Biology, 2001, vol. 46, pp. R1-R45.

Brown "A Survey of Image Registration Techniques," ACM Computing Surveys, Dec. 1992, vol. 24, No. 4, pp. 325-376.

International Search Report and Written Opinion for International (PCT) Patent Application No. PCT/IL2021/051452, dated Mar. 30, 2022, 18 pages.

Extended Search Report for European Patent Application No. 25153837.7, dated Apr. 16, 2025, 7 pages.

* cited by examiner

REGISTRATION OF TIME-SEPARATED X-RAY IMAGES

CROSS REFERENCE TO RELATED APPLICATIONS

This application claims the benefit of U.S. Provisional Application No. 63/125,822, filed on Dec. 15, 2020, and entitled "Registration of Time-Separated X-Ray Images," which application is incorporated herein by reference in its entirety.

FIELD

The present technology generally relates to surgical imaging and navigation, and relates more particularly to tracking anatomical elements before, during, and after surgery.

BACKGROUND

Imaging may be used by a medical provider for diagnostic and/or therapeutic purposes. Patient anatomy can change over time, particularly following placement of a medical implant in the patient anatomy. Registration of one image to another enables changes in anatomical position to be identified and quantified.

SUMMARY

Example aspects of the present disclosure include:

A method comprising: receiving a first image of a patient's anatomy, the first image generated at a first time and depicting a plurality of rigid elements, each of the plurality of rigid elements movable with respect to at least one other of the plurality of rigid elements; receiving a second image of the patient's anatomy, the second image generated at a second time after the first time and depicting the plurality of rigid elements; determining a transformation from the first image to the second image for each one of the plurality of rigid elements to yield a set of transformations; and identifying, using the set of transformations, a common portion of each transformation attributable to a change in camera pose, and an individual portion of each transformation attributable to a change in rigid element pose.

Any of the aspects herein, further comprising: registering the second image to the first image based on the identified common portion of each transformation.

Any of the aspects herein, further comprising: updating a pre-operative model based on the individual portion of each transformation.

Any of the aspects herein, further comprising: updating a registration of one of a robotic space or a navigation space to an image space based on one of the common portion of each transformation or the individual portion of each transformation.

Any of the aspects herein, wherein each transformation is a homography, and the set of transformations is a set of homographies.

Any of the aspects herein, wherein the step of identifying utilizes clustering to isolate transformations in the set of transformations that result from the change in camera pose.

Any of the aspects herein, wherein the step of registering comprises correlating both the first image and the second image to a common vector space.

Any of the aspects herein, wherein the first image is a preoperative image.

Any of the aspects herein, wherein at least one of the first image and the second image is an intraoperative image.

Any of the aspects herein, wherein calculating the transformation comprises identifying at least four points on each one of the plurality of rigid elements as depicted in the first image, and a corresponding at least four points on each one of the plurality of rigid elements as depicted in the second image.

Any of the aspects herein, wherein the first image and the second image are two-dimensional.

Any of the aspects herein, wherein the first image and the second image are three-dimensional.

Any of the aspects herein, wherein the plurality of rigid elements includes a plurality of vertebrae of the patient's spine.

Any of the aspects herein, wherein the plurality of rigid elements comprises at least one implant.

Any of the aspects herein, further comprising: quantifying a change in pose of at least one of the plurality of rigid elements from the first time to the second time.

A method of correlating images taken at different times, comprising: segmenting, in a first image of a plurality of rigid elements taken at a first time and in a second image of the plurality of rigid elements taken at a second time after the first time, each rigid element of the plurality of rigid elements; calculating a homography for each rigid element of the plurality of rigid elements to yield a set of homographies, each homography correlating the rigid element as depicted in the first image to the rigid element as depicted in the second image; arranging the set of homographies into homography clusters based on at least one characteristic; selecting a homography cluster based on at least one parameter; and projecting each of the plurality of rigid elements as depicted in the second image onto the first image using a mean of the selected homography cluster to yield a projection image.

Any of the aspects herein, wherein the second time is at least one month after the first time.

Any of the aspects herein, wherein the second time is at least one year after the first time.

Any of the aspects herein, wherein the at least one parameter is silhouette.

Any of the aspects herein, wherein at least one of the plurality of rigid elements is an implant.

Any of the aspects herein, wherein the plurality of rigid elements includes a plurality of vertebrae of a patient's spine.

Any of the aspects herein, further comprising measuring at least one of an angle or a distance corresponding to a change in pose of one of the plurality of rigid elements as reflected in the projection image.

Any of the aspects herein, further comprising removing, from the set of homographies, any homographies affected by one or more of a compression fracture or a bone osteophyte depicted in the second image but not the first image.

Any of the aspects herein, wherein calculating the homography for each rigid element of the plurality of rigid elements comprises identifying edge points of vertebral end plates.

A system for comparing images, comprising: at least one processor; and a memory. The memory stores instructions for execution by the processor that, when executed, cause the processor to: identify a plurality of elements in a first image generated at a first time; identify the plurality of elements in a second image generated at a second time after the first time; calculate a homography for each one of the plurality of elements, using the first image and the second image, to yield a set of homographies; and determine, based on the set of homographies, a first change in pose of one or more of the plurality of elements in the second image relative to the first image that is attributable to a change in imaging device position, relative to the plurality of elements, from the first image to the second image, and a second change in pose of at least one of the plurality of elements in the second image relative to the first image that is not attributable to the change in imaging device position.

Any of the aspects herein, wherein the memory stores additional instructions for execution by the processor that, when executed, further cause the processor to register the second image to the first image based on the first change in pose.

Any of the aspects herein, wherein the memory stores additional instructions for execution by the processor that, when executed, further cause the processor to update a pre-operative model based on the second change in pose.

Any of the aspects herein, wherein the memory stores additional instructions for execution by the processor that, when executed, further cause the processor to update a registration of one of a robotic space or a navigation space to an image space based on one of the first change in pose or the second change in pose.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Images taken at different points in time of a portion of a patient's anatomy may reflect considerable variability of the structure of the patient's anatomy. This is particularly true where the images are taken pre- and post-operation, and/or when the images are separated by a long period of time, including months or years. For example, the spine structure of a patient following insertion of a spinal rod may differ significantly from the spine structure of the patient prior to insertion of the rod. Moreover, the patient's spine may undergo significant deformation in the weeks, months, and years following insertion of the rod. There is a need to identify and quantify changes in the pose of one or more anatomical elements from a first time at which a first image is taken to a second time at which a second image is taken.

Using changes in the structure of a patient's spine as an example, several factors make regular measurements of such changes incomparable. Such factors may include a change in the pose of the camera(s) or other imaging devices that generate the first and second images; a change in the pose of the patient's anatomy when the first and second images are captured (e.g., a first image may be taken with the patient in a prone or supine position, and a second image may be taken with the patient in a standing position); noise in source labels due to noisy image and/or segmentation errors; and non-rigid transformation of the spine through time or before and after an operation.

Embodiments of the present disclosure utilize corresponding points along the perimeter of each vertebra depicted in the first and second images taken at times t1 and t2, respectively. For example, edge points of the vertebral end plates in AP or LT projections taken at any two times t1 and t2 may be used. The points may be identified manually or automatically.

Due to non-rigid transformation of the spine through time or before and after an operation, direct computation of a transformation between times t1 and t2 are not possible. In other words, because the vertebrae of the spine can move and rotate in different manners, simply comparing changes in the overall spinal structure from time t1 to time t2 does not provide accurate results. Instead, the problem may be treated in the vertebra scope, utilizing the piece-wise rigidity of the spine. Because the motion of each vertebra itself could be assumed to be rigid, a transformation may be computed for each vertebra. Moreover, since the vertebral perimeter can be represented as a plane (end plates, sides, in lateral or anterior projections, for example), a homography transformation H may be a sufficiently useful representation.

According to embodiments of the present disclosure, then, for each vertebra, at least four corresponding points in each image are used to compute homography H parameters. To reduce the noise in the computation, if more points are available, they can be used; classic computer vision methods may be used to automatically fix the labeled corner points; and interpolated points along the labeled lines may be used.

If the spine motion were rigid, then all of the computed homographies {H} would be more or less the same. But, because there is some movement of the individual vertebrae, the computed homographies are expected to be different. Also, noise in labeled points will add noisy homographies.

In light of the foregoing, the set of homographies {H} in the transformation space (whether a 9-dimensional space or a reduced space) may be clustered according to a predetermined characteristic. The most coherent cluster may be selected, and/or the clusters/homographies may be filtered according to other criteria. The mean of the resulting cluster(s) may then be taken as the homography H' between times t1, t2. All vertebra may then be projected from t2 onto t1 using H', and measurements/features may be computed in a more comparable way.

Embodiments of the present disclosure rest on an assumption that bone structure changes over time are less predominant than soft tissue changes over time. Even so, compression fractures and bone osteophyte (spondylophyte) changes can interfere with successful utilization of embodiments of the present disclosure. Where one or more homographies are affected by compression fractures and/or bone osteophytes (and/or other changes to a rigid anatomical element's shape), such homographies may need to be filtered out before the others are averaged or otherwise utilized.

For registration of two-dimensional images, at least four corresponding points are needed, while for registration of three-dimensional images, at least eight corresponding points are needed. In some embodiments, implants themselves may be used instead of or in addition to vertebral endplates or other anatomical features as a source of corresponding points. For example, a rod may provide two corresponding points (e.g., one at each end of the rod), such that two rods, a rod and a screw, or even two screws may be utilized to obtain four corresponding points between the two images. Of course, where one or more implants are to be used to define one or more corresponding points, only pairs of images that both depict the one or more implants may be registered to each other. As a result, images taken before insertion of such implants cannot be used in these embodiments. Even so, using implants to define the corresponding points beneficially takes advantage of the fact that, unlike some anatomical elements, implant structure does not usually change over time.

Embodiments of the present disclosure beneficially enable long term registration—that is, registration of two images generated at times that are separated by a period of weeks, months, or even years. Embodiments of the present disclosure also beneficially utilize the piece-wise rigidity characteristic of the spine (and/or other anatomical elements comprised of a plurality of individual rigid elements) to overcome computational challenges of determining a transformation of the spine or other anatomical element directly. By combining a data science approach with classical computer vision methods, a potential set of transformations can be generated and then analyzed using clustering methods.

Embodiments of the present disclosure provide technical solutions to one or more of the problems of (1) generating and comparing accurate geometric measurements on X-ray images of the same patient, taken at different points in time separated by weeks, months, or even years; (2) during registration of two images taken at two different times and likely by two different imaging devices, (i) accounting for the effect of a change in camera pose relative to patient anatomy from one image to the other, (ii) accounting for the effect of a change in body pose and location from one image to the other, and (iii) accounting for noise in source labels due to noisy image or segmentation errors; (3) registering to each other two spinal images generated at different times despite non-rigid transformation of the spine during the period in between the generation of the first image and the generation of the second image; and (4) differentiating changes in pose of one or more rigid elements depicted in two images that are due to a change in camera pose from those that are due to a change in pose of the one or more rigid elements themselves.

Figure 1:
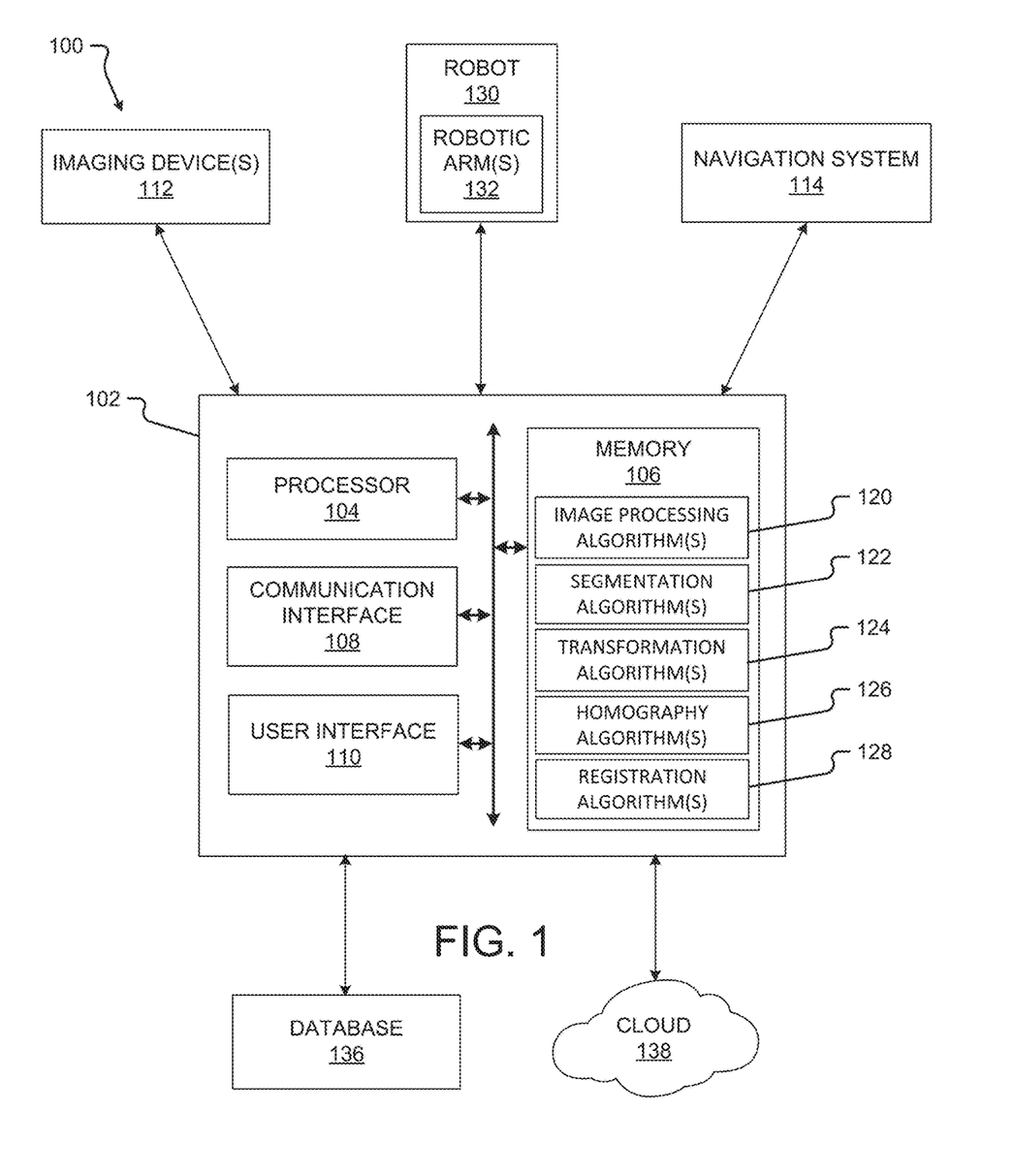
FIG. 1 is a block diagram of a system according to at least one embodiment of the present disclosure.

Turning first to FIG. 1, a block diagram of a system 100 according to at least one embodiment of the present disclosure is shown. The system 100 may be used to register two time-separated images to each other and/or carry out one or more other aspects of one or more of the methods disclosed herein. The system 100 comprises a computing device 102, one or more imaging devices 112, a navigation system 114, a robot 130, a database 136, and/or a cloud 138. Systems according to other embodiments of the present disclosure may comprise more or fewer components than the system 100. For example, the system 100 may not include the navigation system 114, the robot 130, one or more components of the computing device 102, the database 136, and/or the cloud 138.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 130, the navigation system 114, the database 136, and/or the cloud 138.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 300, 400, and/or 500 described herein, or of any other methods. The memory 106 may store, for example, one or more image processing algorithms 120, one or more segmentation algorithms 122, one or more transformation algorithms 124, one or more homography algorithms 126, and/or one or more registration algorithms 128. Such instructions or algorithms may, in some embodiments, be organized into one or more applications, modules, packages, layers, or engines. The algorithms and/or instructions may cause the processor 104 to manipulate data stored in the memory 106 and/or received from or via the imaging device 112, the robot 130, the database 136, and/or the cloud 138.

The computing device 102 may also comprise a communication interface 108. The communication interface 108 may be used for receiving image data or other information from an external source (such as the imaging device 112, the navigation system 114, the robot 130, the database 136, the cloud 138, and/or any other system or component not part of the system 100), and/or for transmitting instructions, images, or other information to an external system or device (e.g., another computing device 102, the navigation system 114, the imaging device 112, the robot 130, the database 136, the cloud 138, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). The image data may be or comprise a pre-operative image, a post-operative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The first time and the second time may be separated by a surgical procedure (e.g., one may be pre-operative, and the other may be post-operative), or by a period of time (e.g., days, weeks, months, or years). The imaging device 112 may be capable of taking a 2D image or a 3D image to yield the image data. "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The imaging device 112 may be or comprise, for example, an ultrasound scanner (which may comprise, for example, a physically separate transducer and receiver, or a single ultrasound transceiver), a radar system (which may comprise, for example, a transmitter, a receiver, a processor, and one or more antennae), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography scanner, an endoscope, a telescope, a thermographic camera (e.g., an infrared camera), or any other imaging device 112 suitable for obtaining images of an anatomical feature of a patient.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The navigation system 114 may provide navigation for a surgeon and/or a surgical robot during an operation. The navigation system 114 may be any now-known or future-developed navigation system, including, for example, the Medtronic StealthStation™ S8 surgical navigation system or any successor thereof. The navigation system 114 may include a camera or other sensor(s) for tracking one or more reference markers, navigated trackers, or other objects within the operating room or other room in which some or all of the system 100 is located. In various embodiments, the navigation system 114 may be used to track a position and orientation (i.e., pose) of the imaging device 112, the robot 130 and/or robotic arm 132, and/or one or more surgical tools (or, more particularly, to track a pose of a navigated tracker attached, directly or indirectly, in fixed relation to the one or more of the foregoing). The navigation system 114 may include a display for displaying one or more images from an external source (e.g., the computing device 102, imaging device 112, or other source) or for displaying an image and/or video stream from the camera or other sensor of the navigation system 114. In some embodiments, the system 100 can operate without the use of the navigation system 114. The navigation system 114 may be configured to provide guidance to a surgeon or other user of the system 100 or a component thereof, to the robot 130, or to any other element of the system 100 regarding, for example, a pose of one or more anatomical elements, and/or whether or not a tool is in the proper trajectory (and/or how to move a tool into the proper trajectory) to carry out a surgical task according to a preoperative plan.

The robot 130 may be any surgical robot or surgical robotic system. The robot 130 may be or comprise, for example, the Mazor X™ Stealth Edition robotic guidance system. The robot 130 may be configured to position the imaging device 112 at one or more precise position(s) and orientation(s), and/or to return the imaging device 112 to the same position(s) and orientation(s) at a later point in time. The robot 130 may additionally or alternatively be configured to manipulate a surgical tool (whether based on guidance from the navigation system 114 or not) to accomplish or to assist with a surgical task. The robot 130 may comprise one or more robotic arms 132. In some embodiments, the robotic arm 132 may comprise a first robotic arm and a second robotic arm, though the robot 130 may comprise more than two robotic arms. In some embodiments, one or more of the robotic arms 132 may be used to hold and/or maneuver the imaging device 112. In embodiments where the imaging device 112 comprises two or more physically separate components (e.g., a transmitter and receiver), one robotic arm 132 may hold one such component, and another robotic arm 132 may hold another such component. Each robotic arm 132 may be positionable independently of the other robotic arm.

The robot 130, together with the robotic arm 132, may have, for example, at least five degrees of freedom. In some embodiments the robotic arm 132 has at least six degrees of freedom. In yet other embodiments, the robotic arm 132 may have less than five degrees of freedom. Further, the robotic arm 132 may be positioned or positionable in any pose, plane, and/or focal point. The pose includes a position and an orientation. As a result, an imaging device 112, surgical tool, or other object held by the robot 130 (or, more specifically, by the robotic arm 132) may be precisely positionable in one or more needed and specific positions and orientations.

In some embodiments, reference markers (i.e., navigation markers) may be placed on the robot 130 (including, e.g., on the robotic arm 132), the imaging device 112, or any other object in the surgical space. The reference markers may be tracked by the navigation system 114, and the results of the tracking may be used by the robot 130 and/or by an operator of the system 100 or any component thereof. In some embodiments, the navigation system 114 can be used to track other components of the system (e.g., imaging device 112) and the system can operate without the use of the robot 130 (e.g., with the surgeon manually manipulating the imaging device 112 and/or one or more surgical tools, based on information and/or instructions generated by the navigation system 114, for example).

The system 100 or similar systems may be used, for example, to carry out one or more aspects of any of the methods 300, 400, and/or 500 described herein. The system 100 or similar systems may also be used for other purposes. In some embodiments, a system 100 may be used to generate and/or display a 3D model of an anatomical feature or an anatomical volume of a patient. For example, the robotic arm 132 (controlled by a processor of the robot 130, the processor 104 of the computing device 102, or some other processor, with or without any manual input) may be used to position the imaging device 112 at a plurality of predetermined, known poses, so that the imaging device 112 can obtain one or more images at each of the predetermined, known poses. Because the pose from which each image is taken is known, the resulting images may be assembled together to form or reconstruct a 3D model. The system 100 may update the model based on information (e.g., segmental tracking information) received from the imaging device 112, as described elsewhere herein.

Figure 2:
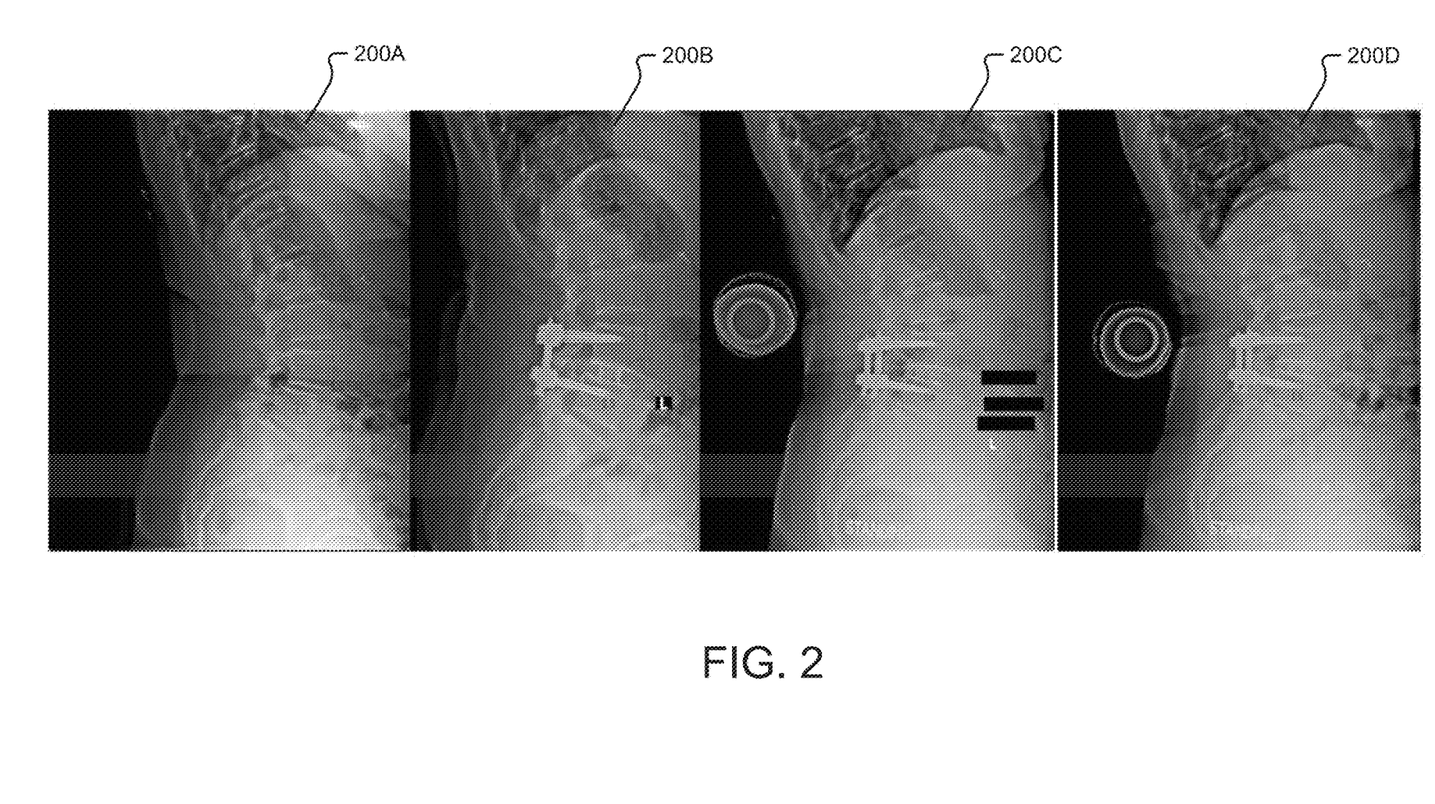
FIG. 2 is a series of X-ray images of a patient's anatomy taken at different times.

Turning now to FIG. 2, embodiments of the present disclosure may be used, for example, to register two images 200 that are separated by time. For example, embodiments of the present disclosure may be used to register a preoperative image 200A to a post-operative image 200B, an image 200C taken six months following the operation, and/or to an image 200D taken one year after the operation; to register a post-operative image 200B to an image 200C taken six months following the operation and/or to an image 200D taken one year following the operation; and/or to register an image 200C taken six months after an operation to an image 200D taken one year after the operation. Additionally, embodiments of the present disclosure may be used to obtain accurate geometric measurements regarding changes in the pose of one or more anatomical elements or medical implants depicted in the registered images, notwithstanding that the images cannot be directly registered to one another (e.g., by simply overlaying one image on another and lining up corresponding points) due to changes in the pose of the camera(s) used to take the images relative to the imaged patient anatomy; changes in the pose of the patient when the images were generated; noise in the images; and/or non-rigid transformation of the anatomy depicted in the images.

While FIG. 2 shows a pre-operative image 200A, a post-operative image 200B taken immediately following the surgical procedure used to implant the rod and screws depicted in image 200B, an image 200C taken six months after the same surgical procedure, and an image 200D taken one year after the same surgical procedure, embodiments of the present disclosure may be used to register two images that are separated by periods of time longer or shorter than from pre-operation to post-operation, six months, and/or one year. In some embodiments, the present disclosure may be utilized to register two images taken two, five, ten, or more years apart. In other embodiments, the present disclosure may be utilized to register two images taken one, two, three, four, five, seven, eight, nine, ten, or eleven months apart. In still other embodiments, the present disclosure may be utilized to register two images taken a period of weeks apart, or a period of days apart. While the benefits of embodiments of the present disclosure may be most pronounced when there is a significant transformation of an imaged anatomical element from one image to the other, those same embodiments may be used regardless of the degree of transformation of an anatomical element between the times at which two images of the anatomical element are taken.

Figure 3:
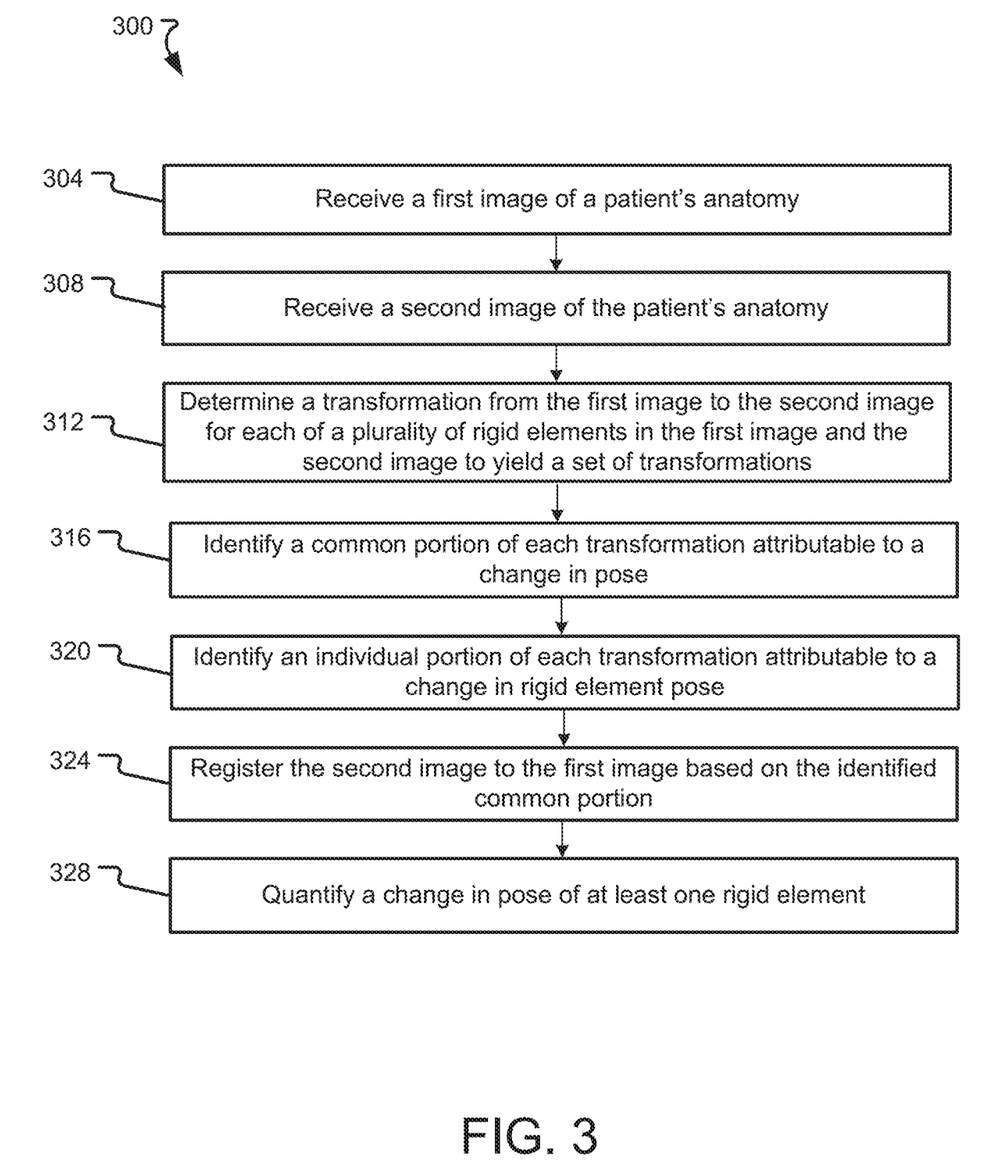
FIG. 3 is a flowchart of a method according to at least one embodiment of the present disclosure.

FIG. 3 depicts a method 300 that may be used, for example, for long-term registration, short-term registration, updating a pre-operative model of a patient's anatomy, and/or updating a registration between any two or more of a robotic space, a navigation space, and/or a patient space. The term "long-term registration" is meant to convey that the method 300 may be used to register to time-separated images, including images that are taken days, weeks, months, or even years apart. Even so, the method 300 may also be used to register images taken in relatively close temporal proximity (e.g., preoperatively and intraoperatively).

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 130) or part of a navigation system (such as a navigation system 114). A processor other than any processor described herein may also be used to execute the method 300. The at least one processor may perform the method 300 by executing instructions stored in a memory such as the memory 106. The instructions may correspond to one or more steps of the method 300 described below. The instructions may cause the processor to execute one or more algorithms, such as an image processing algorithm 120, a segmentation algorithm 122, a transformation algorithm 124, a homography algorithm 126, and/or a registration algorithm 128.

The method 300 comprises receiving a first image of a patient's anatomy (step 304). The first image is generated by an imaging device such as an imaging device 112, and is generated at a first time. The first time may be one or more days, weeks, or months prior to a surgical procedure that affects the imaged anatomy, or the first time may be immediately prior to the surgical procedure (e.g., while the patient is positioned on an operating table and/or is within an operating room), or the first time may be after a surgical procedure. In some embodiments, the first image is taken independently of any surgical procedure.

The imaged anatomy may be, for example, a spine or portion thereof of the patient comprising a plurality of vertebrae. In other embodiments, the imaged anatomy may be any other anatomical object comprised of a plurality of rigid or substantially rigid sub-elements, or any other anatomical object that experiences non-rigid deformation and that can be analyzed on a sub-element level.

The first image may be received, whether directly or indirectly, from an imaging device such as the imaging device 112. The first image may be a two-dimensional image or a three-dimensional image. In some embodiments, the first image is an X-ray image or an image generated using X-rays, such as a CT image or a fluoroscopy image. The image may, however, be an image generated using any other imaging modality, such as ultrasound, magnetic resonance imaging, optical coherence tomography, or another imaging modality. Thus, the imaging device may be a CT scanner, a magnetic resonance imaging (MRI) scanner, an optical coherence tomography (OCT) scanner, an O-arm (including, for example, an O-arm 2D long film scanner), a C-arm, a G-arm, another device utilizing X-ray-based imaging (e.g., a fluoroscope or other X-ray machine), or any other imaging device.

The method 300 also comprises receiving a second image of the patient's anatomy (step 308). The second image is also generated by an imaging device such as an imaging device 112, although the imaging device used to generate the second image may be different than the imaging device used to generate the first image. Moreover, the second image is generated at a second time after the first time. The second time may be separated from the first time by a surgical procedure (e.g., the first image may be a preoperative image and the second image may be a postoperative image). The second time may be separated from the first time by one or more days, weeks, months, or years after the first time.

The second image generally corresponds to the same anatomical area or portion of the patient's anatomy as the first image, or a portion thereof. Thus, for example, if the first image depicts a spine or segment thereof of the patient, then the second image data also depicts the spine or segment thereof. As another example, if the first image depicts a knee or portion thereof of the patient, the second image also depicts the knee or a portion thereof.

The second image may be received, whether directly or indirectly, from an imaging device such as the imaging device 112. The second image may have the same number of dimensions as the first image (e.g., two or three dimensions). The second image may be an image generated using the same imaging device as the first image or a different imaging device. The imaging device that generates the second image may be of the same imaging modality as the imaging device that generated the first image, or a related imaging modality. In some embodiments, the first and second images may be generated using different imaging modalities.

The method 300 also comprises determining a transformation from the first image to the second image for each of a plurality of rigid elements in the first image and the second image, to yield a set of transformations (step 312). The step 312 may comprise, in some embodiments, pre-processing the first image and the second image using one or more image processing algorithms 120 to remove noise and/or artifacts therefrom, ensure that both images have the same scale, and otherwise prepare the image for other aspects of the step 312. One or more image processing algorithms 120 may also be used to identify a plurality of rigid elements in each image, whether using feature recognition, edge detection, or other object-detection methods.

In some embodiments, the step 312 comprises segmenting the first and second images to identify and/or delineate individual rigid elements within each image. Such segmenting may be accomplished using one or more segmentation algorithms 122 and/or any other segmentation algorithm or process. The step 312 may further comprise utilizing an anatomical atlas, biomechanical model, or other reference to identify anatomical objects within the first and second images, determine which of those anatomical objects are rigid elements, and/or to determine a relationship (if any) between or among two or more identified rigid elements. Thus, for example, an anatomical atlas may be referenced to determine that two adjacent vertebra are connected by a vertebral disc, or a patient-specific biomechanical model may be referenced to determine that two adjacent vertebrae have been fused and should move within the patient's anatomy as one.

The plurality of rigid elements may comprise individual bones or other hard tissue anatomical objects. The plurality of rigid elements may further comprise one or more medical implants, such as pedicle screws, vertebral rods, surgical pins, and/or intervertebral bodies. Where a particular rigid element appears in the first image but not the second image, or vice versa, that particular rigid element may be excluded from the plurality of rigid elements. Similarly, the plurality of rigid elements may not include, in some embodiments, every rigid element depicted in one or both of the images. An element of bony anatomy or other hard tissue may be treated as rigid for purposes of the present disclosure even if the element has some degree of flexibility. At least one of the plurality of rigid elements is movable relative to at least one other of the plurality of rigid elements.

To determine the transformation, for each of the plurality of rigid elements, from the first image to the second image, one or more transformation algorithms 124 may be used. The determining may comprise overlaying the second image on the first image or defining any other relationship between the first and second images. In some embodiments, a "best-guess" alignment between the first and second images may be made automatically or manually, such as by aligning a prominent edge or surface in both images (e.g., a visible edge of the patient, such as the patient's back or side; one or more surfaces of a patient's hip or pelvis, or of another hard tissue element that is less likely to move over time than the rigid elements in question). For determining the transformation, a fixed relationship between the two images must be established; however, the fixed relationship need not be accurate, as the remaining steps of the method 300 will distinguish between aspects of each transformation that are attributable to a change in camera pose, patient position, or other parameter that affects the depiction of every rigid element in the same way, and aspects of each transformation that are attributable to movement of the rigid element.

The determined transformation for each of the plurality of rigid elements may be a homography. The homography relates a given rigid element as depicted in the first image to the same rigid element as depicted in the second image. For purposes of calculating the homography, a plurality of points on the rigid element (visible in both the first and second images) may be selected. For example, the points may be points along a perimeter of the rigid element in anterior-posterior (AP) or lateral (LT) projections. Where the rigid element is a vertebra, the points may be edge points of the vertebra end plates. Where the rigid element is a screw, the points may be at the two ends of the screw (e.g., at the top of the screw head and at the screw tip). Where the rigid element is a rod, the points may be at opposite ends of the rod. Multiple screws in a single anatomical element may be treated as a single rigid element for purposes of the present disclosure. The points may be designated manually (e.g., via a user interface such as the user interface 110) or automatically (e.g., using an image processing algorithm 120, a segmentation algorithm 122, or any other algorithm). The homography may be calculated using a homography algorithm such as the homography algorithm 126. Any known method for calculating homographies may be used.

In some embodiments, a homography may be calculated for adjacent rigid elements. Thus, for example, a homography may be calculated for each pair of adjacent vertebrae, using the determined transformations corresponding to each pair of adjacent vertebrae.

Where the first and second images are two-dimensional images, the plurality of points comprises at least four points. Where the first and second images are three-dimensional images, the plurality of points comprises at least eight points. Whether 2D or 3D images are being used, more points may be utilized than the minimum number of points. Additionally, the needed points may comprise points defined with referenced to the patient's anatomy, points defined with reference to one or more implants (e.g., screws, rods), or any combination thereof. The selected points may be connected by labeled lines, and one or more points may be interpolated along the labeled lines. Notably, noise in the points used to calculate the homographies (e.g., any discrepancy between the location of the point in each image relative to the corresponding rigid element in the image) will contribute to the calculation of noisy homographies.

Use of screws, rods, and/or other implants as rigid elements for purposes of the present disclosure is beneficial given that such implants may be less likely to change over time than anatomical elements.

The determination of a transformation (whether a homography or otherwise) for each of the plurality of rigid elements results in a set of transformations. Each transformation may comprise one or more distances, angles, and/or other measurements sufficient to describe a change in pose of the rigid element for which the transformation was determined. In some embodiments, each determined transformation may simply comprise a segmented image of the rigid element in a first position (e.g., as depicted in the first image) and in a second position (e.g., as depicted in the second image). In still other embodiments, the determined transformation may comprise an equation or a set of equations that describe the movement of the rigid element from a pose depicted in the first image to a pose depicted in the second image.

The method 300 also comprises calculating a homography for each transformation.

The method 300 also comprises identifying a common portion of each transformation attributable to a change in pose (step 316). The identifying may be based, for example, on the calculated transformations. Based on an assumption that most of the transformations will be determined only by a change in camera pose (e.g., because the corresponding vertebrae or other rigid elements have not moved), or alternatively that identical or nearly identical transformations result from a change in camera pose (which affects each rigid element more or less equally, while the motion of an individual rigid element does not necessarily have any correlation to the motion of the other rigid elements), a clustering data science approach may be used to isolate the transformations that originate only from camera pose from those transformations that result from a combination of change in camera pose as well as from motion of the rigid element.

Where clustering is used, the clustering may be completed in the transformation space (e.g., a 9-dimensional space) or a reduced space. The resulting clusters may be analyzed using silhouette measure, variance, size or another parameter useful for separating those transformations attributable to a change in camera pose from those attributable both to a change in camera pose and to motion of the rigid element. The most coherent cluster (or the cluster selected by application of the other parameter) may be averaged, with the mean of that cluster being taken as the transformation corresponding to the change in camera pose. The use of clustering beneficially accounts for noise in the transformations resulting from noise in the labeled points used to calculate the transformations.

The transformation corresponding to the change in camera pose may explain the motion of most individual rigid elements in the first image and the second image. Regardless of the number of rigid elements whose transformations are explained solely by a change in camera pose, the portion of each transformation that is explained solely by the change in camera pose constitutes the common portion of each transformation (e.g., because it affects each transformation equally).

Regardless of how the step 316 is completed, the result thereof is a determination of how a change in pose of the camera(s) used to take the first and second images contributes to the determined transformation of each rigid element.

The method 300 also comprises identifying an individual portion of each transformation attributable to a change in rigid element pose (step 320). The identifying an individual portion of each transformation attributable to a change in rigid element pose may comprise, for example, utilizing the common portion of each transformation determined in the step 316 to project each rigid element from the second image onto the first image. The result of this projection will be to align the rigid elements depicted in the second image that did not move between the first time and the second time with the corresponding rigid element depicted in the first image. For rigid elements that did move between the first time and the second time, however, the result of the projection will be to remove the effect of the change in camera pose from the depiction of the rigid element. As a result, any misalignment between the rigid element as projected from the second image onto the first image and the corresponding rigid element as depicted in the first image is attributable to movement of the rigid element itself. In other words, any difference between the pose of the rigid element as projected from the second image onto the first image and the corresponding rigid element as depicted in the first image constitutes the individual portion of each transformation attributable to a change in rigid element pose.

In some embodiments, the identifying may not comprise projecting the rigid elements from the second image onto the first image using the common portion of each transformation determined in the step 316. Instead, the identifying may comprise calculating a difference between the common portion of each transformation determined in the step 316 and the transformation calculated for the individual rigid element. In some embodiments, any such calculated difference that falls below a predetermined threshold may be discarded as attributable to noise or otherwise constituting immaterial movement. Other methods of identifying an individual portion of each transformation attributable to a change in rigid element pose may also be utilized according to embodiments of the present disclosure.

The method 300 also comprises registering the second image to the first image based on the identified common portion (step 324). The step 324 may occur prior to the step 320 (among other steps) and may comprise projecting the rigid elements from the second image onto the first image using the common portion of each transformation identified in the step 316. The registering may also comprise otherwise aligning the second image with the first image based on elements known not to have moved from the first time to the second time (e.g., elements that only appear to have moved due to the change in camera pose, but which in fact have not moved (or have not moved within a particular tolerance). The registering may utilize one or more registration algorithms, such as the registration algorithms 128.

In some embodiments, the step 324 may alternatively comprise updating a preoperative model based on the individual portion of each transformation. The pre-operative model may have been generated, for example, based on a preoperative image, and the updating may comprise updating each rigid element depicted in the pre-operative model to reflect any changes in position of that rigid element from the time the preoperative image was taken to the time the second image was taken. In such embodiments, the second image may be an intraoperative image or a postoperative image.

Also in some embodiments, the step 324 may alternatively comprise updating a registration of one of a robotic space or a navigation space to an image space based on one of the common portion of each transformation or the individual portion of each transformation. The updating may facilitate maintenance of an accurate registration, which may in turn increase the accuracy of a surgical procedure.

The method 300 also comprises quantifying a change in pose of at least one rigid element (step 328). The quantifying utilizes only the portion of each transformation attributable to a change in rigid element pose. In other words, the quantifying comprises quantifying one or more aspects of the change in pose of a particular rigid element resulting from movement of the rigid element from the first time to the second time (as opposed to an apparent change in pose of the particular rigid element attributable to the change in pose of the camera(s) used to image the rigid element at the first time and the second time).

The quantifying may comprise, for example, determining an angle of rotation of the rigid element from the first time to the second time, and/or determining a translation distance of the rigid element. The quantifying may comprise comparing pose of the rigid element at the second time to a desired change in pose, and may be expressed as a percentage of a desired change in pose (e.g., based on a comparison to a physical or virtual model of an ideal pose of the rigid element, whether in a surgical plan, a treatment plan, or otherwise). The quantifying may further comprise quantifying the change in pose of each of the rigid elements.

The present disclosure encompasses embodiments of the method 300 that comprise more or fewer steps than those described above, and/or one or more steps that are different than the steps described above.

Figure 4:
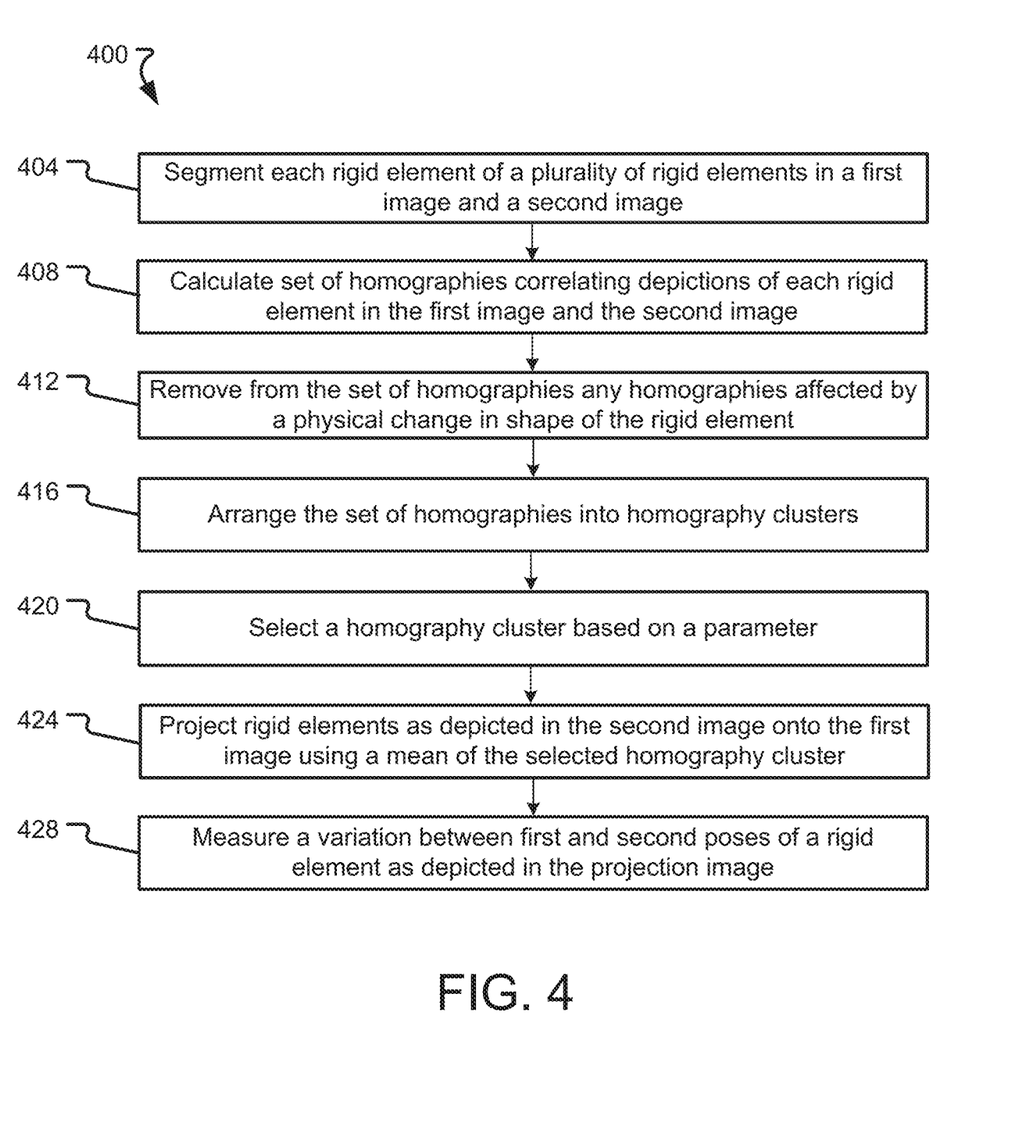
FIG. 4 is a flowchart of another method according to at least one embodiment of the present disclosure.

FIG. 4 depicts a method 400 for correlating images taken at different times. The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 130) or part of a navigation system (such as a navigation system 114). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as an image processing algorithm 120, a segmentation algorithm 122, a transformation algorithm 124, a homography algorithm 126, and/or a registration algorithm 128.

The method 400 comprises segmenting each of a plurality of rigid elements in a first image and in a second image (step 404). The first image is taken at a first time, and the second image is taken at a second time after the first time. The first image may be the same as or similar to any other first image described herein, and the second image may be the same as or similar to any other second image described herein. The first and second images each depict a common portion of an anatomy of a patient, although the first and second images may not be perfectly aligned (e.g., in addition to the common portion of the patient's anatomy depicted in both the first image and the second image, the first image may depict one or more portions of the anatomy of the patient not depicted in the second image and vice versa). The plurality of rigid elements may be or comprise, for example, one or more vertebrae and/or other bony anatomy or hard tissue elements, and/or one or more implants (e.g., pedicle screws, cortical screws, rods, pins, and/or other implants).

The segmenting may be accomplished using one or more segmentation algorithms 122 and/or any other segmentation algorithm or process. The step 312 may further comprise utilizing an anatomical atlas, biomechanical model, or other reference to identify anatomical objects within the first and second images, determine which of those anatomical objects are rigid elements, and/or to determine a relationship (if any) between or among two or more identified rigid elements. Thus, for example, an anatomical atlas may be referenced to determine that two adjacent vertebra are connected by a vertebral disc, or a patient-specific biomechanical model may be referenced to determine that two adjacent vertebrae have been fused and should move within the patient's anatomy as one. The segmenting enables determination of the perimeter of each rigid element in the first and second images, such that each rigid element can be individually analyzed.

The method 400 also comprises calculating a set of homographies correlating the depiction of each rigid element in the first image to the corresponding rigid element in the second image (step 408). The homographies may be calculated using any known method. The calculating may utilize one or more homography algorithms 126. Each calculated homography may describe a relationship between a rigid element in the first image and the corresponding rigid element in the second image. In other words, each homography relates a rigid element in the first image to a corresponding rigid element in the second image. Stated differently, using the calculated homography as well as a depiction of a rigid element in either the first image or the second image, the depiction of the rigid element in the other of the first image or the second image may be generated.

For purposes of calculating the homographies, a plurality of points on each rigid element (visible in both the first and second images) may be selected. For example, the points may be points along a perimeter of the rigid element in anterior-posterior (AP) or lateral (LT) projections. Where the rigid element is a vertebra, the points may be edge points of the vertebra end plates. Where the rigid element is a screw, the points may be at the two ends of the screw (e.g., at the top of the screw head and at the screw tip). Where the rigid element is a rod, the points may be at opposite ends of the rod. Multiple screws in a single anatomical element may be treated as a single rigid element for purposes of the present disclosure. The points may be designated manually (e.g., via a user interface such as the user interface 110) or automatically (e.g., using an image processing algorithm 120, a segmentation algorithm 122, or any other algorithm). The homography may be calculated using a homography algorithm such as the homography algorithm 126. Any known method for calculating homographies may be used.

Where the first and second images are two-dimensional images, the plurality of points comprises at least four points. Where the first and second images are three-dimensional images, the plurality of points comprises at least eight points. Whether 2D or 3D images are being used, more points may be utilized than the minimum number of points. Additionally, the needed points may comprise points defined with referenced to the patient's anatomy, points defined with reference to one or more implants (e.g., screws, rods), or any combination thereof. The selected points may be connected by labeled lines, and one or more points may be interpolated along the labeled lines. Notably, noise in the points used to calculate the homographies (e.g., any discrepancy between the location of the point in each image relative to the corresponding rigid element in the image) will contribute to the calculation of noisy homographies.

Use of screws, rods, and/or other implants as rigid elements for purposes of the present disclosure is beneficial given that such implants may be less likely to change over time than anatomical elements.

The method 400 also comprises removing from the set of homographies any homographies affected by a physical change in shape of the rigid element (step 412). The method 400 is based on an assumption that bone structure changes (and rigid element shape changes more generally) are less predominant than soft tissue changes, any rigid elements that have changed in shape will add undesirable noise. Changes in shape of rigid elements do sometimes occur, however. Such change in shape may result, for example, from compression fractures, bone osteophytes (spondylophytes), and/or other causes.

The removing of homographies affected by a physical change in shape may be completed manually or automatically. In some embodiments, changes in shape may be identified by a treating physician or other user (from the first and second images, for example) prior to calculation of any homographies. In other embodiments, a treating physician or other user may review the first and second images after the homographies have been calculated, and may identify one or more rigid elements that have changed in shape, based upon which identification the corresponding homographies may be discarded or ignored. In still other embodiments, changes in shape may be identified by a processor using one or more image processing algorithms 120 or other algorithms, whether prior to or after the segmenting of the step 404. In such embodiments, changes in shape may be identified based on a rough comparison of the edges of each rigid element (e.g., as detected using an edge detection algorithm, a segmenting algorithm, or otherwise) in the first image and the second image.

The method 400 also comprises arranging the set of homographies into homography clusters (step 416). The homographies may be clustered using any data science clustering approach. The purpose of the clustering is to identify those homographies that are most similar, which can be assumed to correspond to rigid elements that have not moved from the first time to the second time, but whose change in pose in the second image relative to the first image can be attributed entirely or almost entirely to a change in camera pose. Thus, any clustering approach may be used that results in similar homographies being grouped together. The clustering may be completed in the transformation space (e.g., a 9-dimensional space) or a reduced space.

The method 400 also comprises selecting a homography cluster based on a parameter (step 420). The parameter may be silhouette, variance, size or another parameter useful for separating those homographies attributable to a change in camera pose from those attributable both to a change in camera pose and to motion of the rigid element. The cluster may comprise a majority of the homographies utilized in the cluster analysis, or a minority of such homographies. Because a change in camera pose (e.g., from the first time to the second time) will affect each rigid element equally (while motion of each rigid element will not necessarily be correlated to motion of any other rigid element), the most coherent cluster is most likely to comprise homographies that reflect only perceived motion resulting from that change in camera pose. Even the most coherent cluster, however, is unlikely to have perfectly matching homographies, due to noise in the homographies resulting from noise in the labeled points used to calculate the homographies, the segmenting of each rigid element, and any other aspects of the method 400 that may lack 100% accuracy.

The method 400 also comprises projecting each rigid element as depicted in the second image on the first image, using a mean of the selected homography cluster, to yield a projection image (step 424). The mean of the selected homography is utilized to reduce the impact of any noise that affected the homographies in the most coherent (or other selected) cluster. The mean of the selected homography is then used to project the rigid elements from the second image onto the first image. Because the selected homography corresponds to the effect of the change in pose of the camera(s) from the first time (when the first image was captured) to the second time (when the second image was captured), the projecting results in any projected rigid elements that did not move from the first time to the second time being aligned with and overlapping the corresponding rigid element from the first image. For any rigid element that did move from the first time to the second time, the projecting of such rigid elements will remove any effect from the change in camera pose on the pose of the such projected rigid elements, such that the projection image depicts only the actual change in pose of such rigid elements from the first time to the second time.

The method 400 also comprises measuring a variation between the first and second poses of a rigid element as depicted in the projection image (step 428). As described above, the projection image comprises images of each rigid element from the second image that have been projected onto the first image using a mean of the selected homography. As a result, any variation in pose between two corresponding anatomical elements in the projection image may be assumed to reflect an actual change in pose of the rigid element. Such change in pose may be measured, thus yielding one or more angles of rotation, distances of translation, and/or other parameters describing the movement of the rigid element from the first time to the second time. In some embodiments, the measured quantities may be compared to a desired quantity (as reflected, for example, in a treatment plan) to yield a percent of achievement or similar parameter. In other embodiments, the measured quantities may be compared to the amount of time separating the first time from the second time to yield a rate of change, which may be used to predict future changes in pose of the one or more rigid elements, to predict if and when additional surgery or other treatment will be needed, or for any other useful purpose.

Additionally, the measured quantity (and/or the results of any calculations completed using the measured quantity) may be displayed to a treating physician or other user on a user interface such as the user interface 110. The measured quantity may be displayed as a number, or may be converted into an indicator (e.g., a red indicator where the quantity is within a predetermined range of unacceptable values, a yellow indicator where the quantity is within a predetermined range of unsatisfactory values, and a green indicator where the quantity is within a predetermined range of acceptable values).

The present disclosure encompasses embodiments of the method 400 that comprise more or fewer steps than those described above, and/or one or more steps that are different than the steps described above.

Figure 5:
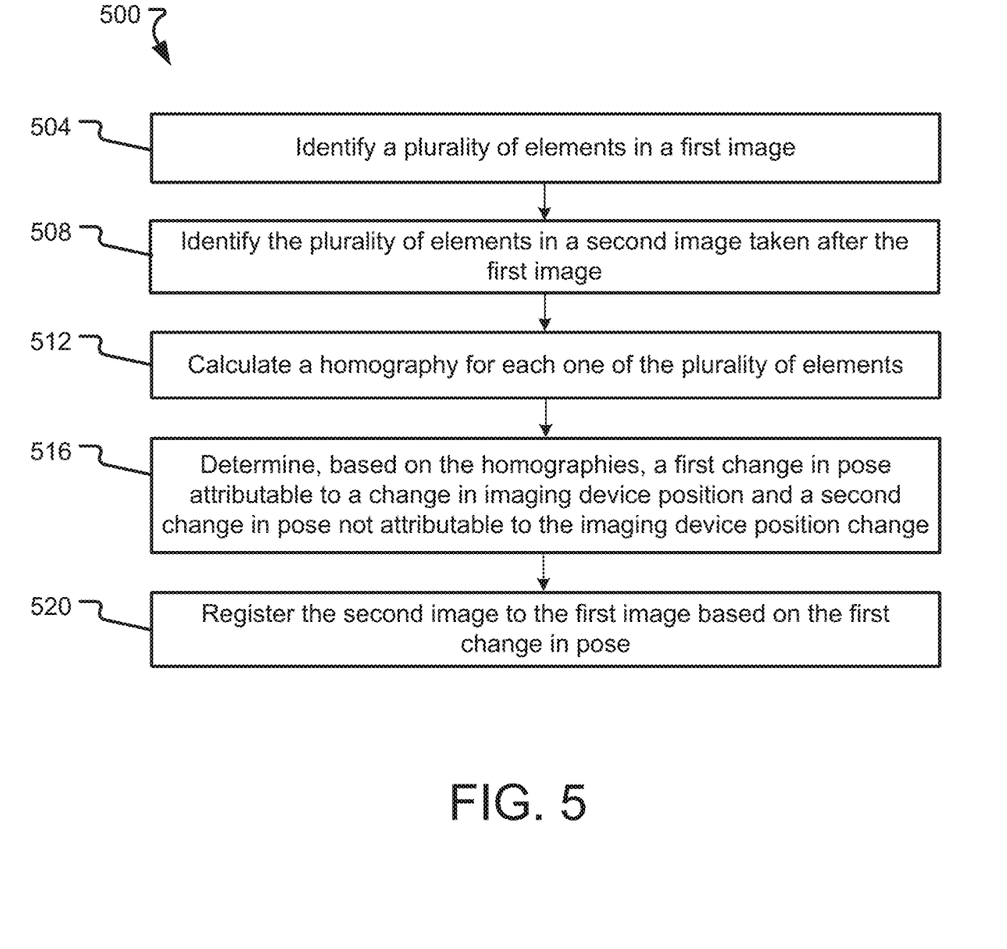
FIG. 5 is a flowchart of another method according to at least one embodiment of the present disclosure.

FIG. 5 depicts a method 500 for comparing images. The method 500 (and/or one or more steps thereof) may be carried out or otherwise performed, for example, by at least one processor, which may be part of a system. The at least one processor may be the same as or similar to the processor(s) 104 of the computing device 102 described above. The at least one processor may be part of a robot (such as a robot 130) or part of a navigation system (such as a navigation system 114). A processor other than any processor described herein may also be used to execute the method 500. The at least one processor may perform the method 500 by executing instructions stored in a memory such as the memory 106. The instructions may correspond to one or more steps of the method 500 described below. The instructions may cause the processor to execute one or more algorithms, such as an image processing algorithm 120, a segmentation algorithm 122, a transformation algorithm 124, a homography algorithm 126, and/or a registration algorithm 128.

The method 500 comprises identifying a plurality of elements in a first image (step 504). The first image may be taken using any imaging device (e.g., an imaging device 112), and is taken at a first time. The first image depicts a portion of a patient's anatomy. The identifying may utilize one or more image processing algorithms, such as the image processing algorithms 120. Each of the elements is a rigid element, and may be an anatomical rigid element (e.g., a bony anatomy or hard tissue element) or a rigid implant (e.g., a screw, a rod, a pin). The plurality of elements may include both one or more anatomical rigid elements and one or more rigid implants. In some embodiments, the identifying the plurality of elements in the first image also comprises segmenting the plurality of elements in the first image, which may be accomplished in any manner described herein or in any other known manner of segmenting elements in an image.

The method 500 also comprises identifying the plurality of elements in a second image taken after the first image (step 508). Like the first image, the second image may be taken using any imaging device (e.g., an imaging device 112), and depicts the same portion of the patient's anatomy as the first image (or at least a substantially overlapping portion of the patient's anatomy). The second image is taken at a second time after the first time. As with other embodiments of the present disclosure, the second time may be days, weeks, months, or even years after the first time. The identifying may utilize one or more image processing algorithms, such as the image processing algorithms 120. The plurality of elements identified in the second image is the same plurality of elements identified in the first image. In some embodiments, the identifying the plurality of elements in the second image also comprises segmenting the plurality of elements in the second image, which may be accomplished in any manner described herein or in any other known manner of segmenting elements in an image.

The method 500 also comprises calculating a homography for each one of the plurality of elements (step 512). The step 512 is the same as or similar to the step 316 of the method 300 and/or the step 408 of the method 400.

The method 500 also comprises determining, based on the homographies, a first change in pose attributable to a change in imaging device position, and a second change in pose not attributable to the imaging device position change (step 516). The step 516 is the same as or similar to a combination of the steps 316 and 320 of the method 300, and/or a combination of the steps 416, 420, and 424 of the method 400.

The method 500 also comprises registering the second image to the first image based on the first change in pose (step 520). The step 520 is the same as or similar to the step 324 of the method 300.

In some embodiments, the step 520 may alternatively comprise updating a preoperative model based on the individual portion of each transformation. The pre-operative model may have been generated, for example, based on a preoperative image, and the updating may comprise updating each rigid element depicted in the pre-operative model to reflect any changes in position of that rigid element from the time the preoperative image was taken to the time the second image was taken. In such embodiments, the second image may be an intraoperative image or a postoperative image.

Also in some embodiments, the step 520 may alternatively comprise updating a registration of one of a robotic space or a navigation space to an image space based on one of the common portion of each transformation or the individual portion of each transformation. The updating may facilitate maintenance of an accurate registration, which may in turn increase the accuracy of a surgical procedure.

The present disclosure encompasses embodiments of the method 500 that comprise more or fewer steps than those described above, and/or one or more steps that are different than the steps described above.

As noted above, the present disclosure encompasses methods with fewer than all of the steps identified in FIGS. 3, 4, and 5 (and the corresponding description of the methods 300, 400, and 500), as well as methods that include additional steps beyond those identified in FIGS. 3, 4, and 5 (and the corresponding description of the methods 300, 400, and 500). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method comprising:
   receiving a first image of a patient's anatomy, the first image generated at a first time and depicting a plurality of rigid elements, each of the plurality of rigid elements movable with respect to at least one other of the plurality of rigid elements;
   receiving a second image of the patient's anatomy, the second image generated at a second time after the first time and depicting the plurality of rigid elements;
   determining a transformation from the first image to the second image for each one of the plurality of rigid elements to yield a set of transformations; and
   identifying, using the set of transformations, a common portion of each transformation attributable to a change in camera pose by utilizing clustering to isolate transformations in the set of transformations that result solely from the change in camera pose from transformations in the set of transformations that result from a combination of the change in camera pose and the change in rigid element pose; and
   identifying, using the set of transformations, an individual portion of each transformation attributable to a change in rigid element pose by utilizing the clustering.

2. The method of claim 1, further comprising:
   registering the second image to the first image based on the identified common portion of each transformation.

3. The method of claim 1, further comprising:
   updating a pre-operative model based on the individual portion of each transformation.

4. The method of claim 1, further comprising:
updating a registration of one of a robotic space or a navigation space to an image space based on one of the common portion of each transformation or the individual portion of each transformation.

5. The method of claim 1, wherein each transformation is a homography, and the set of transformations is a set of homographies.

6. The method of claim 1, wherein the step of identifying comprises determining a most coherent cluster and using a mean of the most coherent cluster as a transformation corresponding to the change in camera pose in a step of projecting the second image onto the first image.

7. The method of claim 1, wherein the step of registering comprises correlating both the first image and the second image to a common vector space.

8. The method of claim 1, wherein the first image is a preoperative image.

9. The method of claim 1, wherein at least one of the first image and the second image is an intraoperative image.

10. The method of claim 1, wherein determining the transformation comprises identifying at least four points on each one of the plurality of rigid elements as depicted in the first image, and a corresponding at least four points on each one of the plurality of rigid elements as depicted in the second image.

11. The method of claim 1, wherein the first image and the second image are two-dimensional.

12. The method of claim 1, wherein the first image and the second image are three-dimensional.

13. The method of claim 1, wherein the plurality of rigid elements includes a plurality of vertebrae of the patient's spine.

14. The method of claim 1, wherein the plurality of rigid elements comprises at least one implant.

15. The method of claim 1, further comprising quantifying a change in pose of at least one of the plurality of rigid elements from the first time to the second time.

16. A system, comprising:
at least one processor; and
a memory storing instructions for execution by the processor that, when executed, cause the processor to:
receive a first image of a patient's anatomy, the first image generated at a first time and depicting a plurality of rigid elements, each of the plurality of rigid elements movable with respect to at least one other of the plurality of rigid elements;
receive a second image of the patient's anatomy, the second image generated at a second time after the first time and depicting the plurality of rigid elements;
determine a transformation from the first image to the second image for each one of the plurality of rigid elements to yield a set of transformations; and
identify, using the set of transformations, a common portion of each transformation attributable to a change in camera pose by utilizing clustering to isolate transformations in the set of transformations that result solely from the change in camera pose from transformations in the set of transformations that result from a combination of the change in camera pose and the change in rigid element pose; and
identify, using the set of transformations, an individual portion of each transformation attributable to a change in rigid element pose by utilizing the clustering.

17. The system of claim 16, wherein the memory stores instructions for execution by the processor that, when executed, cause the processor to:
register the second image to the first image based on the identified common portion of each transformation.

18. The system of claim 16, wherein the memory stores instructions for execution by the processor that, when executed, cause the processor to:
update a pre-operative model based on the individual portion of each transformation.

19. The system of claim 16, wherein the memory stores instructions for execution by the processor that, when executed, cause the processor to:
update a registration of one of a robotic space or a navigation space to an image space based on one of the common portion of each transformation or the individual portion of each transformation.

20. The system of claim 16, wherein the memory stores instructions for execution by the processor that, when executed, cause the processor to:
determine a most coherent cluster and using a mean of the most coherent cluster as a transformation corresponding to the change in camera pose in a step of projecting the second image onto the first image.

* * * * *